United States Patent [19]

Kumarathasan et al.

[11] Patent Number: 5,840,966
[45] Date of Patent: Nov. 24, 1998

[54] HYDROXYLATION OF SALICYLIC ACID DERIVATIVES

[75] Inventors: Premkumari Kumarathasan, Ottawa; Renaud Vincent, Aylmer, both of Canada

[73] Assignee: Minister of Health and Welfare, Ottawa, Canada

[21] Appl. No.: 734,578

[22] Filed: Oct. 17, 1996

[51] Int. Cl.$^6$ .................................................. C07C 227/16
[52] U.S. Cl. ............................................ 562/453; 424/9.1
[58] Field of Search ................................ 562/453; 424/9.1

[56] References Cited

U.S. PATENT DOCUMENTS 3,931,295 1/1976 Massie ...................................... 562/453

OTHER PUBLICATIONS

Dull et al, Biochem Pharm., vol. 36, #15, pp. 2467–2472, 1987.

*Primary Examiner*—James H. Reamer
*Attorney, Agent, or Firm*—George A. Seaby

[57] ABSTRACT

The invention disclosed relates to the novel compound 5-amino tetrahydroxy benzoic acid and derivatives thereof, e.g. pharmaceutically acceptable acid addition salts, to a process for the preparation thereof which involves reacting 5-amino salicylic acid with hydroxyl radical, and to a method of using 5-amino tetrahydroxy benzoic acid and derivatives thereof as a biomarker for the presence of hydroxyl radical in biological systems.

6 Claims, 6 Drawing Sheets

HPLC Chromatogram
FENTON REACTION 1. 5-AmSA
2. 5-ATHBA
3. 2,3 DHBA
4. 2,5 DHBA
5. Salicylic Acid HPLC Chromatogram
IMPINGER HPLC Chromatogram
PLASMA 1. 5-AmSA  2. 5-ATHBA
3. 2,3 DHBA  4. 2,5 DHBA
5. Salicylic Acid  6. 5-amino-2-hydroxy-N-N'-bis(3-carboxy-4-hydroxyphenyl)-1,4-benzoquinonediimide

HYDROXYLATION OF SALICYLIC ACID DERIVATIVES

BACKGROUND OF THE INVENTION

1. Field of the Invention

This invention relates to the novel compound 5-amino tetrahydroxy benzoic acid, a process for its preparation, and to a method of using this novel compound as a biomarker to detect the presence of hydroxyl radical in biological systems.

2. Description of the Prior Art

Free radicals are at the centre of mechanisms of tissue injury in inflammatory diseases and in biological effects of chemicals and ionizing radiation. One of the most potent free radicals is the hydroxyl radical. It is known to damage almost all molecules, including DNA and membrane lipids.

The hydroxyl radical can also be generated when the reduced forms of various transition metal ions come into contact with hydrogen peroxide. In probably the most biologically relevant of these reactions, the so-called Fenton reaction, divalent iron is the catalyst, typically in the form of a salt such as sulfate and chloride. The problem is the detection of the short-lived hydroxyl radical molecule in biological systems.

Various prior art methods for the detection of hydroxyl radical are described in Halliwell, Barry et al., Methods for the Measurement of Hydroxyl Radical in Biochemical Systems: Deoxyribose Degradation and Aromatic Hydroxylation, Methods of Biochemical Analysis, Vol. 33, pp. 59–89, 1989.

Aromatic hydroxylation for the detection of the hydroxyl radical in biological systems is exemplified by hydroxylation of salicylate. Prior art studies have described the in vivo hydroxylation of salicylic acid to 2,3-dihydroxy benzoic acid, a metabolite not expected from monooxygenase hydroxylation. For exaizple, in Liu, Ling et al., Hydroxylation of Salicylate in the Lungs of Fischer 344 Rats: Effects of Aging and Ozone Exposure, Am. J. Physiol. (Lung Cell. Mol. Physiol.), In Press, the metabolite 2,3-diydroxy benzoic acid was measured in plasma of rats which had been exposed by inhalation to the oxidant ozone.

Several prior art studies of the oxidative degradation products of 5-amino salicylic acid (5-AMSA) have also been reported. For example, in Dull, Bob Jay et al., 5-Aminosalicylate: Oxidation by Activated Leukocytes and Protection of Cultured Cells from Oxidative Damage, Biochem. Pharm. Vol. 36, No. 15, pp. 2467–2472, 1987, 5-AMSA is reacted with hydroxyl radical generated from a Fenton reaction. However, only two metabolites were identified, namely, salicylate (5-ASA) and gentisate (2,5-dihydroxy benzoic acid).

SUMMARY OF THE INVENTION

We have used ozonation and Fenton reactions in vitro in an aqueous environment to create several hydroxylation products of 5-amino salicylic acid. The products were then separated by high pressure liquid chromatography (HPLC) with electrochemical detection. Analyte peaks eluted from the chromatographic column were derivatized by silylation by conventional means, then studied by gas chromatography and mass spectrometry, and the fragmentation patterns were analyzed.

We have discovered a hydroxylation product of 5-amino salicylic acid, which we have identified as 5-amino tetrahydroxy benzoic acid, consisting of an aromatic ring substituted at position 1 by a carboxyl group, at position 5 by an amino group, and at positions 2, 3, 4, and 6 by hydroxyl groups. The product only appears to be conceivable by reaction with hydroxyl radicals.

We have also injected rats in vivo with 5-amino salicylic acid, and have exposed the animals to ozone by inhalation. We have then verified the presence of the compound 5-amino tetrahydroxy benzoic acid (5-AMTHBA) in the lungs and plasma of the animals. Accordingly, we have proved that this compound can be formed by reaction with the hydroxyl radical, and that it can be measured in biological samples after a treatment which causes an oxidative stress in tissues.

In the synthesis of 5-AMTHBA, the compounds 5-amino 2,3-dihydroxy benzoic acid, 5-amino 2,3,6-trihydroxy benzoic acid, and 5-amino 2,3,4-trihydroxy benzoic acid are possible intermediates.

Derivatized products of 5-AMTHBAL, obtained by chemical or metabolic means, and their measurement in biological materials or samples by immunological, chemical and physical methods, are also involved in this invention. For exale, the aforementioned silylation products. Other useful derivatives include its pharmaceutically acceptable acid addition salts. Because 5-AMTHBA is substituted with an amino group and a carboxyl group, it can also be derivatized with haptens by conventional means in order to produce polyclonal anti-sera or monoclonal antibodies.

Moreover, a novel, simple, specific, sensitive bio-indicator of the hydroxyl radical is provided. One application of the invention could be in the prognosis of inflammatory diseases, such as inflammatory bowel disease or arthritis, in order to evaluate the improvement or deterioration of the patient's condition. Another application is in the estimation of inflammatory and free radical reactions induced by exposure to oxidants, such as ozone, and physical agents such as ionizing radiation, in which the hydroxyl radical is thought to play a role. A further application could be in a dosimeter for the irradiation of biological materials.

DESCRIPTION OF THE PREFERRED EMBODIMTS

Hydroxylation of salicylic acid derivatives

Figure 1:
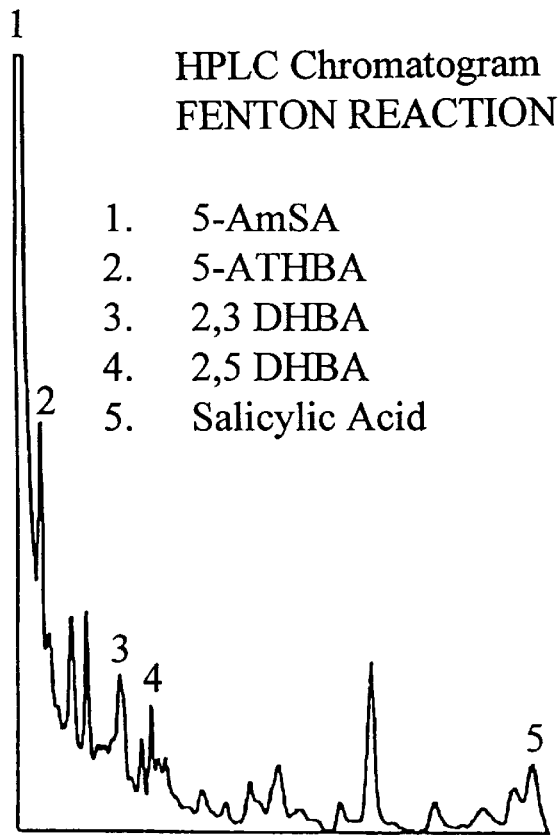
FIG. 1 is a HPLC chromatogram illustrating the reaction products of the in vitro Fenton reaction derived products of 5-AMSA and hydroxyl radical, produced from reduction of hydrogen peroxide by iron.

It is well known that salicylate hydroxylation by the hydroxyl radical yields 2,3- and 2,5-dihydroxy benzoic acid (DHBA). Furthermore, as 2,5-DHBA is also formed by enzymatic hydroxylation of salicylic acid, the product 2,3-DHBA has the potential to be useful as a marker in the assessment of hydroxyl radical formation in a system. In our previous work we have established that 2,3-DHBA could be used to assess hydroxyl radical formation during ozone exposure of rats. Since 2,5-DHBA is the major product in vivo compared to its 2,3-DHBA analogue during salicylate hydroxylation and has an enzymatic origin in addition to direct aromatic ring hydroxylation, and since it is conceivable that 2,3-DHBA could result from modification of 2,5-DHBA, specificity of 2,3-DHBA as a biomarker of hydroxyl radical can be questioned. Derivatives of salicylic acid were therefore investigated to overcome this problem and to determine their eventual potential in the assessment of hydroxyl radical formation.

5-amino salicylic acid (5-AMSA) was chosen for the assessment of hydroxyl radical formation because the amino group at position 5 blocks the enzyme assisted hydroxylation at this position, and by means of steric hindrance reduces the possibility of any other enzyme assisted hydroxylations on the aromatic ring. Furthermore, it is a better free radical scavenger compared to salicylic acid, and could be used at lower doses compared to salicylic acid to probe the hydroxyl radical with the current assay conditions. It is used in the treatment of rheumatoid arthritis and ulcerative colitis.

In vitro and in vivo formation of hydroxyl radical adducts of 5-AMSA were investigated for the selection of a probe to assess radical formation. Furthermore, adducts of hydroxylation products of 5-AMSA to protein were created, and the adducts were subsequently hydrolysed from the protein and identified in HPLC chromatograms.

In Vitro

1. Fenton Reaction:

Samples:

A solution containing 1 mM $Fe^{2+}$(as sulfate) and 100 $\mu$M 5-amino salicylic acid in 0.9% saline was treated with $H_2O_2$ (final concentration, 1 mM).

Reaction conditions:

37° C. for 1 hour; reaction was quenched with 1N HCl on ice.

2. Ozone Reaction in Impingers:

Samples:

A. Solution containing 100 $\mu$M 5-amino salicylic acid in 0.9% saline.

B. Solution containing 100 $\mu$M 5-amino salicylic acid and 1 mM $Fe^{2+}$in 0.9% saline.

Reaction conditions:

Solutions A or B in impingers were exposed to 2 ppm ozone for 2 hours at room temperature (21±1° C.); reaction was quenched with 1N HCl on ice.

3. Formation of Protein Adducts in vitro:

Samples:

A solution containing 100 $\mu$M 5-amino salicylic acid and 1 mM $Fe^{2+}$(as sulfate) in 0.9% saline were exposed along with plasma sample from Fisher 344 rat in impinger to ozone.

Reaction conditions:

2 ppm $O_3$ for 2 h; reaction was quenched with 1N HCl on ice.

In Vivo

1. Animals:

Male, Fischer 344 rats (B. Wt.: 200–250 g) were trained for 2 hours per day for 5 consecutive days prior to the exposure experiments in nose-only exposure tubes.

2. Ozone Exposures:

Thirty minutes prior to ozone exposure, the animals were injected intraperitoneally with 50 mg 5-AMSA per kg body weight. Animals were exposed to ozone for 2 hours in a custom-made 8-port teflon manifold. Ozone was generated (1 or 2 ppm) through a silent-arc generator, model 200 (Erwin Sander, Uetze, Germany). Stable ozone concentrations were maintained with less than 2% variability.

3. Samples:

The animals were killed and 0.9% saline was introduced intratracheally for broncho-alveolar lavage. Blood was obtained.

Lung lavage fluid, blood samples (in heparinized tubes) and lung tissue samples were treated with BHT (butylatedhydroxytoluene-antioxidant), DETP (diethylenetriaminepentaacetic acid-metal chelator) and sucrose. The lavage and plasma samples were stored on ice and the lung tissue samples were frozen in liquid nitrogen. The lavage samples were centrifuged and filtered, and the liquid was analyzed for hydroxylation products of 5-AMSA. Lung tissue samples were homogenized in two volumes of 10% trichloroacetic acid and centrifuged, and the supernatants were analyzed for hydroxylation products of 5-AMSA. Plasma samples were treated with an equal volume of 10% TCA(trichloroacetic acid) and centrifuges, and the supernatants were analyzed for hydroxylation products of 5-AMSA.

ANALYSES

HPLC-ECD

Sample Preparation:

Samples were treated with NaCl (0.1 g/mL), extracted with ethyl acetate, and evaporated with a flow of nitrogen. The samples were reconstituted with acidified deionized water (water:1N HCl=4:1) and filtered (0.045 mm).

Analysis Conditions:

Mobile phase was sodium citrate buffer (pH 4.75) at a flow rate of 1 ml/min. The column was a reversed phase C-18, 25 cm, 4.6 i.d., 5 $\mu$m particle size. Electrochemical detection was used at an oxidation potential of +0.94V.

GC-MS

Sample Preparation:

HPLC samples or the fractions collected from HPLC runs were extracted into ethyl acetate, evaporated under a flow of nitrogen, and silylated with a mixture of trimethylchlorosilane, hexamethyldisilazane, and pyridine in a ratio of 1:3:9 to obtain the corresponding trimethyl silyl derivatives.

Analysis Conditions:

A DB-5 column was used (25 m, 0.25 mm i.d., 0.1 $\mu$m film thickness).

The temperature program was 80° C. for 1 min, 10° C. per min to 300° C., 20 min at 300° C. ITD conditions were ionization by EI mode (emission current, 10 $\mu$A; electron multiplier voltage, 1650 V); scan range, 40–650 amu; scan rate, 1 $sec^{-1}$.

Analysis of protein adducts:

Plasma samples were treated with equal volumes of 10% TCA, vortexed and centrifuged to remove supernatants for HPLC analysis (sample prep. for HPLC analysis is given under analysis section). The precipitates were washed with 10% TCA (twice) and were extracted with ethylacetate.

Ethylacetate soluble fractions (sample prep. for HPLC analysis is given under analysis section) were analyzed by HPLC.

The insoluble part of the precipitate in aqueous phase was then dried in the oven at 60° C. for ca. 2.5 h, then treated with 1N NaOH solution and maintained at 60° C. for 1 h in a hot water bath.

Samples were treated with 1N HCl for extraction by ethyl acetate and analysis by HPLC (sample prep. for HPLC analysis is given under analysis section).

Brief Results

Figure 2:
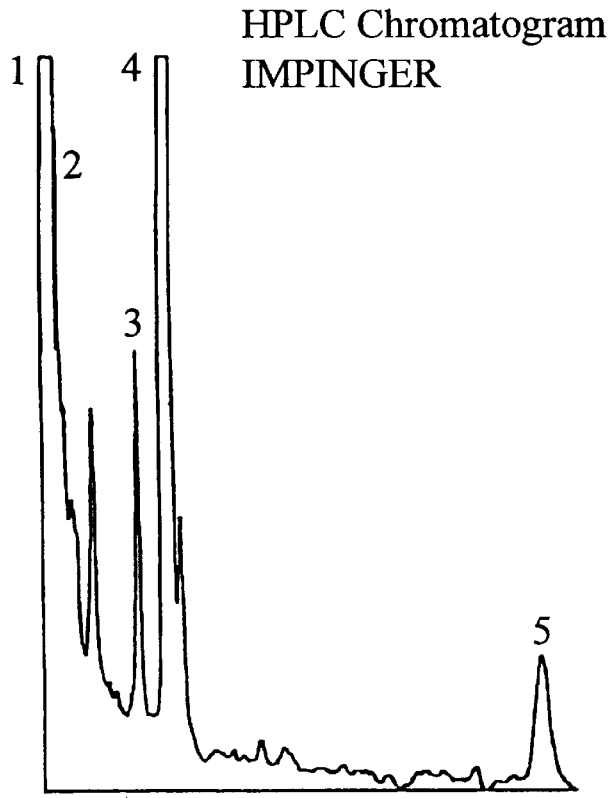
FIG. 2 is a HPLC chromatogram illustrating hydroxylation products of 5-AMSA after in vitro ozone reaction in an impinger.

FIGS. 1 and 2 show that 5-AMTHBA, is formed from the reaction of 5-AMSA with the hydroxyl radical generated in a classical Fenton reaction (FIG. 1) or from ozone in an aqueous milieu (FIG. 2).

In FIG. 1, Peak 1: an amount of the parent compound 5-AMSA (elution time ca. 4.2 min) is recovered. Peak 2: the hydroxylation product 5-ATHBA is resolved (4.6 min). Peak 3: the product 2,3-DHBA is also monitored (7.2 min). Peak 4: 2,5-DHBA is also detected (8.2 min). Peak 5: deamination of 5-AMSA also produces salicylic acid (21.2 min).

In FIG. 2, Peak 1: 5-AMSA (4.2 min). Peak 2: 5-ATHBA, (4.6 min). Peak 3: 2,3-DHBA (7.2 min). Peak 4: 2,5-DHBA (8.2 min). Peak 5: salicylic acid (21.2 min).

Figure 3:
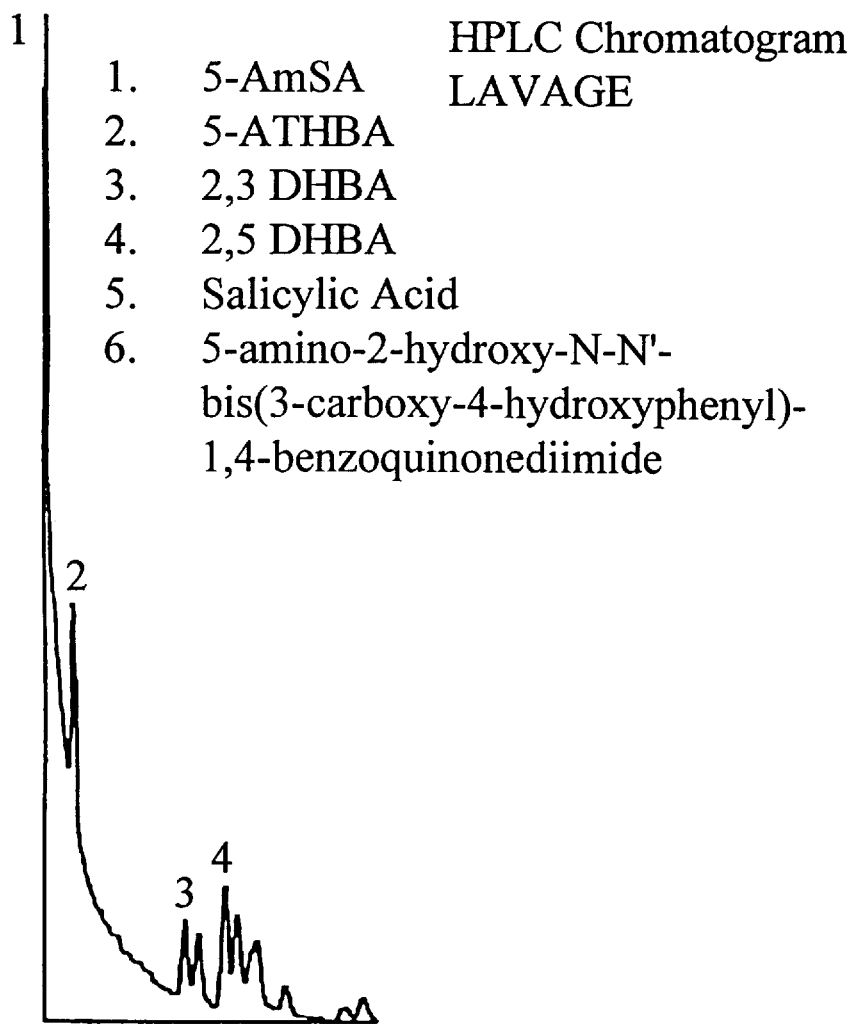
FIG. 3 is a HPLC chromatogram of material recovered in broncho-alveolar lavage fluids from animals after injection of 5-AMSA followed by inhalation exposure to ozone.
Figure 4:
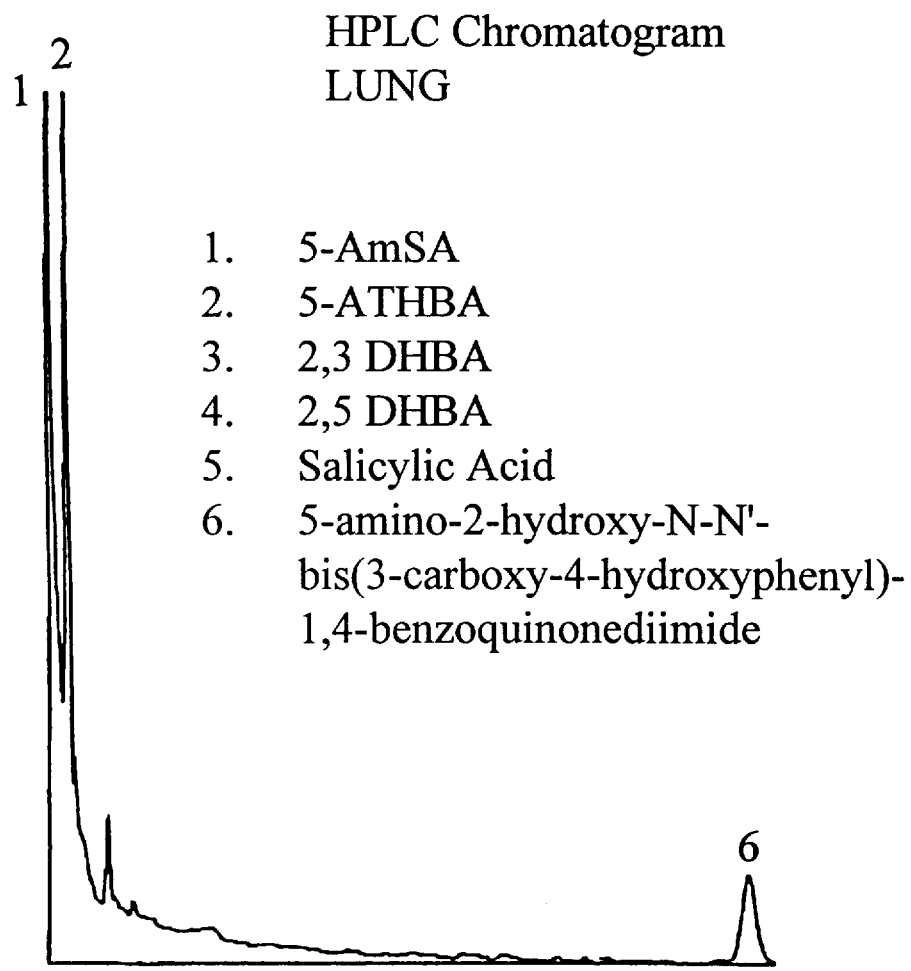
FIG. 4 is a HPLC chromatogram of rat lung samples after in vivo ozone exposure.
Figure 5:
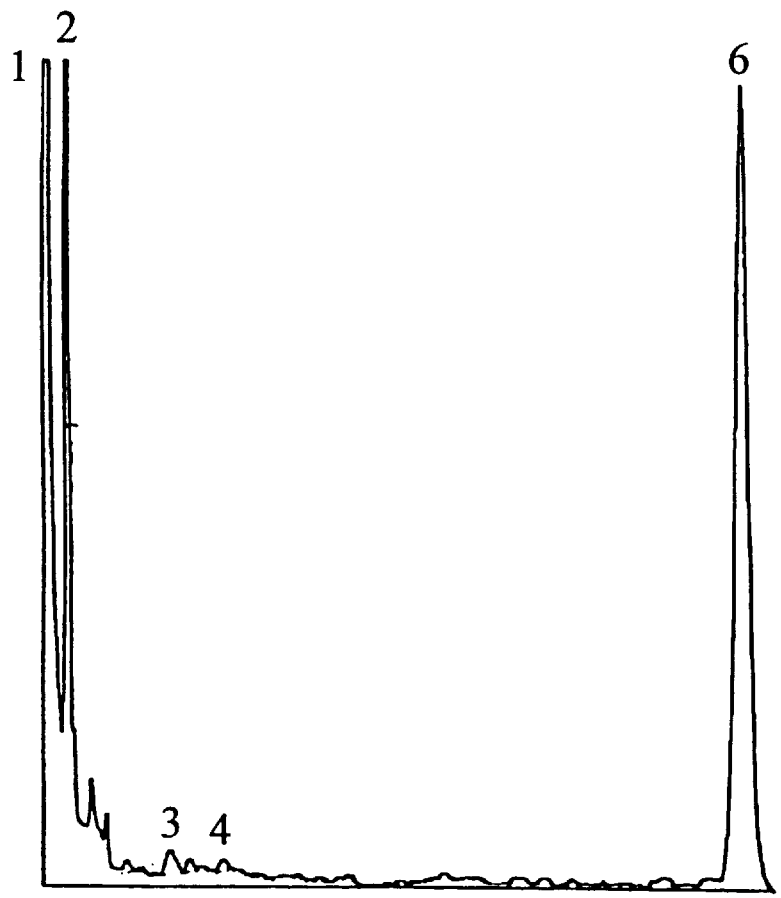
FIG. 5 is a HPLC chromatogram of rat plasma samples after in vivo ozone exposure.

FIGS. 3–5 show that the product 5-AMTHBA can be recovered from biological material after creation of an oxidative stress in animals. Notably, the figures indicate that 5-AMTHB is a more sensitive indicator of the hydroxyl radical than the 2,3-DHBA and 2,5-DHBA metabolites generated from reorganization of ring substituents. Furthermore, the detection of 5-AMTHBA in plasma indicate that this product could be used to monitor oxidative stress occurring at different locations in the body.

In FIG. 3, Peak 1: 5-AMSA (4.2 min). Peak 2: 5-ATHBA (4.6 min). Peak 3: 2,3-DHBA (7.2 min). Peak 4: 2,5-DHBA (8.2 min). Peak 5: salicylic acid (21.2 min). Peak 6: 5-amino-2-hydroxy-N-N'-bis(3-carboxy-4-hydroxyphenyl)-1,4-benzoquinonediimide (25.9 min).

In FIG. 4, Peak 1: 5-AMSA (4.2 min). Peak 2: 5-ATHBA (4.6 min). Peak 3: 2,3-DHBA (7.2 min). Peak 4: 2,5-DHBA (8.2 min). Peak 6: 5-amino-2-hydroxy-N-N'-bis (3-carboxy-4-hydroxyphenyl)-1,4-benzoquinonediimide (25.9 min) is a condensation product of oxidized 5-AMSA.

In FIG. 5, Peak 1: 5-AMSA (4.2 min). Peak 2: 5-ATHBA, (4.6 min). Peak 6: 5-amino-2-hydroxy-N-N'-bis(3 carboxy-4-hydroxyphenyl)-1, 4-benzoquinonediimide (25.9 min).

Figure 6:
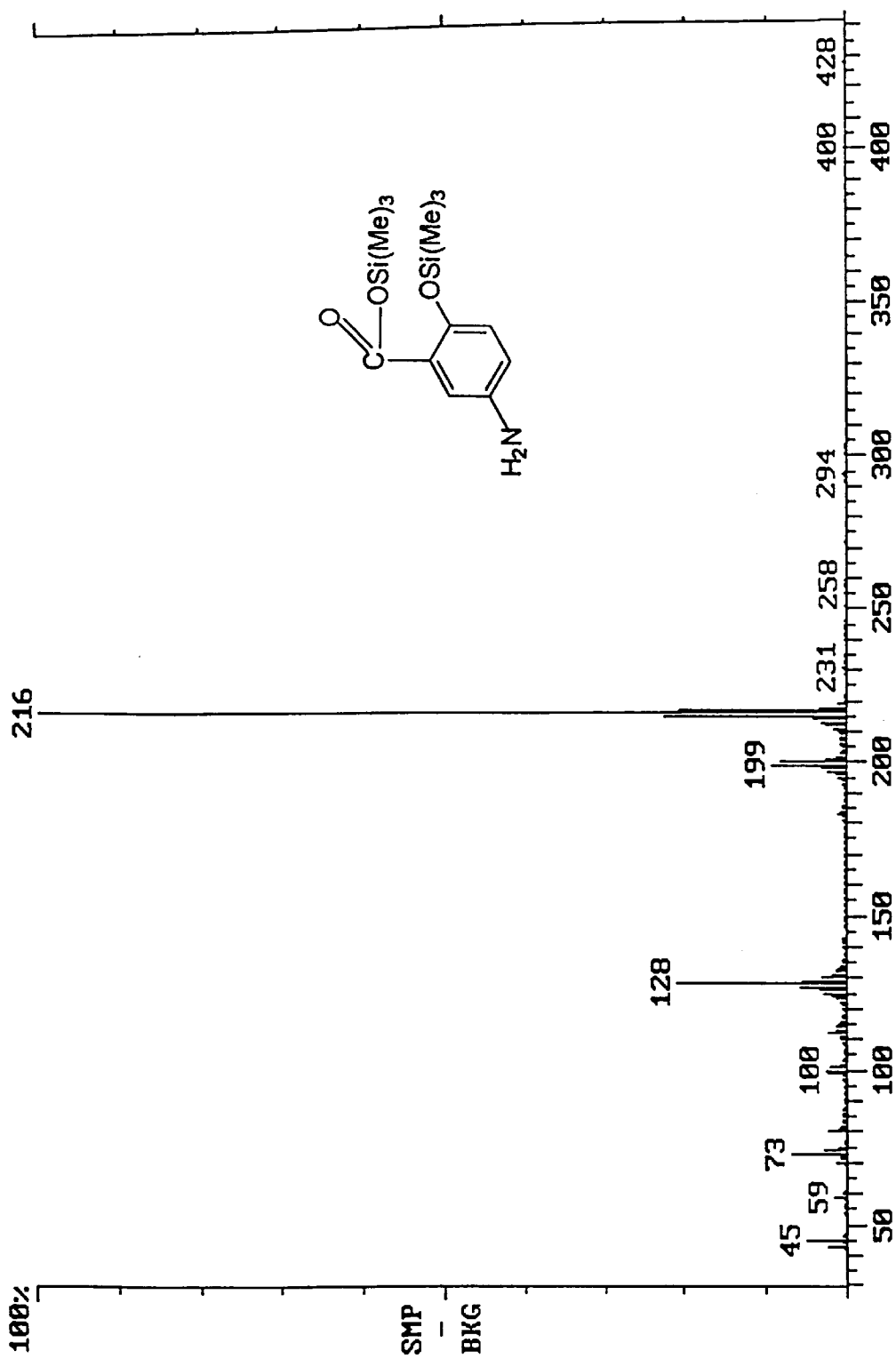
FIG. 6 is the GC-MS fragmentation pattern of trimethyl silyl derivative of 5-amino salicylic acid (5-AmSA).
Figure 7:
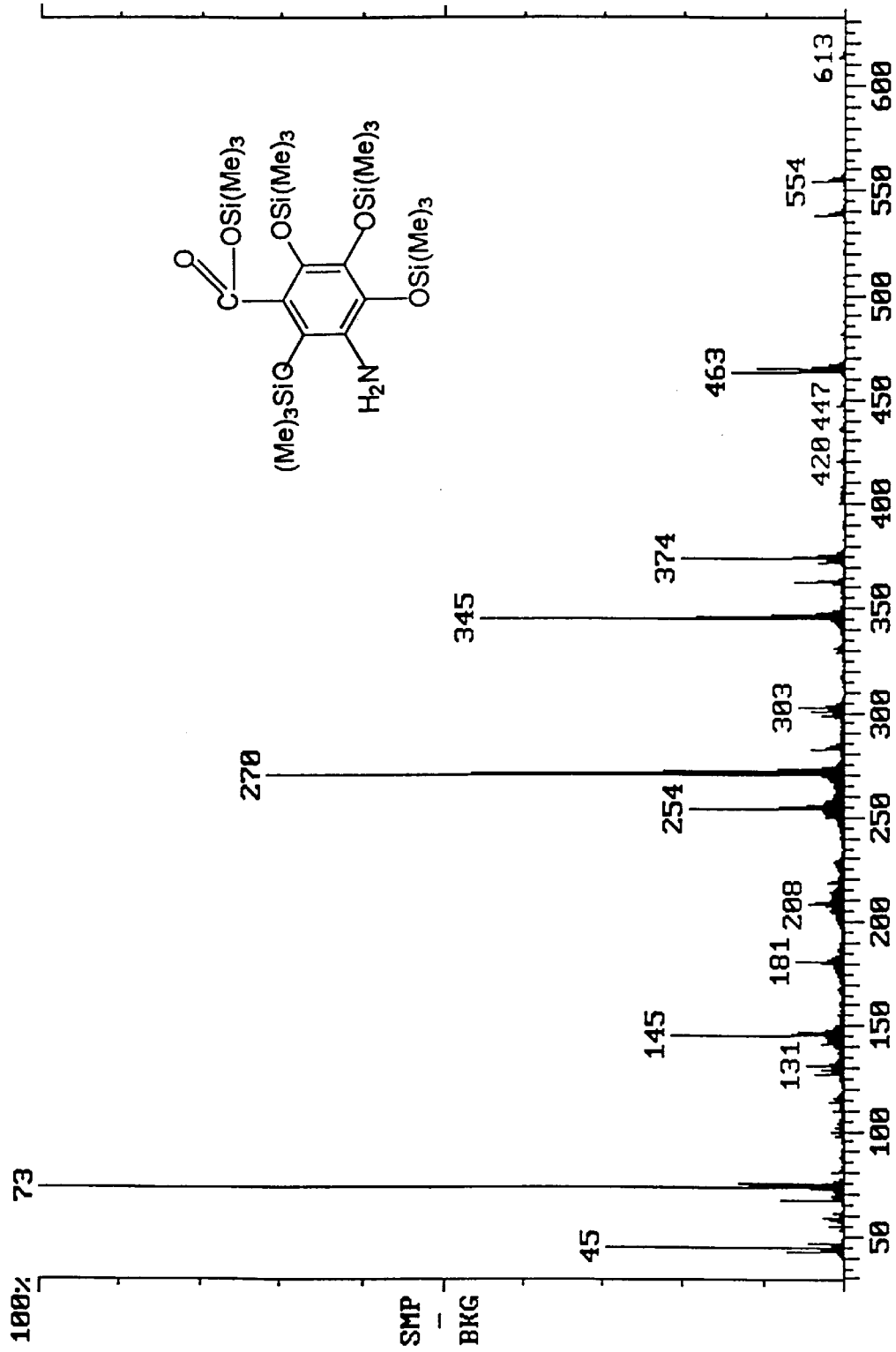
FIG. 7 is the GC-MS fragmentation pattern of trimethyl silyl derivative of 5-amino tetrahydroxy benzoic acid (5-ATHBA)).

FIGS. 6 and 7 illustrate the gas chromatography-mass spectrometry fragmentation patterns of products recovered in HPLC chromatogram elution peaks after separation of samples obtained from biological materials. These figures identify the molecular structure of the silyl derivatives of the parent compound 5-AMSA and the hydroxylation product 5AMTHBA.

In FIG. 6, identical patterns are obtained for standard 5-AMSA, and for peak 1 of the HPLC elution of biological samples as well as in vitro reaction samples.

In FIG. 7, identical patterns are obtained for peak 2 of the HPLC elution of in vitro reaction samples as well as from plasma samples or lung lavage samples of animals exposed to ozone.

More specifically, both in vitro Fenton and ozone reactions in impingers yielded the same types of hydroxylated products including 5-amino tetrahydroxy benzoic acid (5-AMTHBA), 2,3-dihydroxy benzoic acid (2,3 -DHBA), 2,5-DHBA, and salicylic acid (see FIGS. 1–2). Structural assignment of 5-AMTHBA is made based on the GC-MS analysis of the corresponding trimethyl silyl derivative (FIGS. 6–7). The identity of 2,3-DHBA, 2,5-DHBA, salicylate, and 5-AMSA was confirmed by the corresponding reference standards by HPLC and GC methods. Iron ($Fe^{2+}$) in the presence of $H_2O_2$ leads to the formation of hydroxyl radical according to the classical Fenton reaction. $Fe^{2+}$ did not seem to affect the ozonation reactions very much except for the shifts in the spectrum of reaction products. $H_2O_2$ is probably the rate limiting factor under these conditions. In systems with sufficient $H_2O_2$, equimolar amounts of $Fe^{2+}$ would be necessary to obtain optimum amounts of hydroxyl radical and thus optimum formation of 5-AMTHBA. Other transition metal ions such as ($Cu^+$) could also be used. As much as 50% of the 5-AMSA can be converted to 5-ATHBA by Fenton reaction.

In the in vivo experiments, the hydroxylation product 5-ATHBM was the major product formed compared with the 2,3-DHBA and 2,5-DHBA. 5 -AMTHBA was detected in lung lavage fluid, lung tissue, and plasma of animals exposed to ozone (FIGS. 3–5). Because reactive intermediates are formed, covalent binding of reaction products can also be expected. When 5-AMSA was reacted with ozone in a solution containing protein and $Fe^{2+}$, $^5$-AMTHBA could be recovered in solution. Proteins were precipitated and the ethylacetate wash of the precipitate prior to the hydrolysis procedure did not exhibit peak 2 in the HPLC analysis. However, after protein hydrolysis, 5-AMHBA could be recovered from the protein precipitate and measured by HPLC-ECD. This indicated that adducts can also be created in biological systems. Monitoring of hydroxyl radical also includes measurement of free 5-AMTHBA as well adducts of 5-AMTHBA to macromolecules. Immunological methods are well suited.

Accordingly, the antibody to a protein adduct of 5 -amino-tetrahydroxybenzoic acid can be made up into a test kit for determining the presence of the hydroxyl radical in a biological system, said kit comprising a supply of the antibody, a developing agent for indicating the presence of the antibody and hence the hydroxyl radical, and means enabling a sample from said biological system to be exposed to the antibody. A supply of purified protein adduct for use as a standard, and equipment normally associated with antibody test kits e.g. dipstick, blot or ELISA material and suitable instructions would also be typically included.

We claim:

1. A method for the detection of hydroxyl radical in an aqueous biological system, comprising adding to the system a non-toxic amount of 5-amino salicylic acid, and assaying the hydroxylation products so formed for the presence of 5-aminotetrahydroxy benzoic acid.

2. A method according to claim 1 wherein the biological system is an in vivo system, selected from body fluids, tissues and plasma.

3. A test kit for determining the presence of hydroxyl ion in an aqueous biological system, comprising a supply of antibody capable of binding to a protein adduct of 5-amino-tetrahydroxy benzoic acid, a developing agent for indicating the presence of said antibody and hence the hydroxyl ion, and means for enabling a sample from the biological system to be exposed to the antibody.

4. A test kit according to claim 3, wherein the biological system is an in vivo system selected from body fluids, tissue and plasma.

5. A method according to claim 1, wherein the assaying step includes separating and detecting the presence of 5-aminotetrahydroxy benzoic acid in the hydroxylation products, by chromatographic and electrochemical detection means.

6. A method to claim 5, wherein the chromatographic means is high performance liquid chromatography.

* * * * *